United States Patent [19]
Kaplan

[11] Patent Number: 5,989,529
[45] Date of Patent: Nov. 23, 1999

[54] SUBSTANTIVE TOPICAL COMPOSITION

[75] Inventor: Carl Kaplan, Memphis, Tenn.

[73] Assignee: Schering-Plough Healthcare Products, Inc., Memphis, Tenn.

[21] Appl. No.: 09/208,091

[22] Filed: Nov. 20, 1998

[51] Int. Cl.$^6$ .............................. A61K 7/42; A61K 7/44; A61K 7/00; A61K 31/74

[52] U.S. Cl. .............................. 424/59; 424/60; 424/400; 424/401; 424/78.02; 424/78.03; 424/78.17; 514/937; 514/938

[58] Field of Search .............................. 424/59, 60, 400, 424/401, 78.02, 78.08, 78.17; 514/937, 938

[56] References Cited

U.S. PATENT DOCUMENTS

| | | | |
|---|---|---|---|
| 4,522,807 | 6/1985 | Kaplan | 424/59 |
| 5,585,104 | 12/1996 | Ha et al. | 424/401 |
| 5,736,125 | 4/1998 | Morawsky et al. | 424/59 |

FOREIGN PATENT DOCUMENTS 695027  8/1998  Australia .

OTHER PUBLICATIONS

ICI Surfactants Product Bulletin Code No. 80152 ARLACEL® P135, ICI Americas, Inc. Wilmington, DE (Apr., 1995).

ARLACEL™ P135, Cosmetics And Toiletries Manufacturing Worldwide, Aston Publishing Group (1997).

ARLACEL® P135—"Wafer In Oils—The Next Generation" ICI Surfactants (1998).

ARLACEL® P135 Polymeric Emulsifier Product Brochure, ICI Surfactants (1996).

*Primary Examiner*—Shelley A. Dodson
*Attorney, Agent, or Firm*—Edward H. Mazer

[57] ABSTRACT

A dermatologically compatible substantive oil-in-water sunscreen composition is disclosed comprising a block polymer substantive agent and a sunscreening agent. The composition is adaptable for dispensing by a spray means.

25 Claims, No Drawings

SUBSTANTIVE TOPICAL COMPOSITION

BACKGROUND OF THE INVENTION

The present invention relates to dermatologically acceptable highly substantive oil-in-water emulsions. More specifically the present invention relates to an improved oil-in-water sunscreen composition. In a preferred embodiment, the sunscreen may be dispensed by a spray means.

There has been a long recognized need for a vehicle which is highly substantive, i.e. highly resistant to removal by water. Such a vehicle would be of particular interest in a sunscreen composition for use by bathers or any other persons whose occupation or life-style make it necessary to be exposed to the actinic rays of the sun.

In many countries, sunscreen formulations comprising oil-in-water emulsions, in which the feel is influenced by the aqueous phase during application, are preferred to water-in-oil emulsions, which have the feel of the oil phase.

Many of the sunscreen compositions which have been known heretofore have been relatively viscous and must be poured from the container into the hands for manual application to the body. In some commercial formulations having reduced viscosity, phase separation has occurred. Emulsions which have had relatively low viscosities frequently are not stable and have tended to separate into an oil phase and a water phase.

Accordingly, it would be desirable to provide an improved substantive oil-in-water emulsion having acceptable emulsion stability and adherence to the body so that it will not be easily removed by contact with water. The product should also exhibit cosmetic elegancy.

Australian Patent Publication No. 695,027 discloses the use of a water-in-oil emulsion comprising at least one oxyethylenated and oxypropylenated polyalkylpolyethersiloxane and at least one polymer exhibiting water-in-oil emulsifying properties. The emulsifier preferably is a polyhydroxylated block polymer with a polyethylene glycerol having 30 ethylene oxide units being particularly preferred.

We have found that a substantive agent comprising a block polymer containing poly(hydroxylated ester) blocks and polyethylene glycol blocks, such as PEG 30 dipolyhydroxystearate, has surprising utility in oil-in-water emulsions, particularly sunscreen compositions. We also surprisingly have found that the combination of this substantive agent with sunscreens permits the formulation of an improved oil-in-water sunscreen formulation having improved stability, low viscosity and cosmetic elegancy.

SUMMARY OF THE INVENTION

The present invention is directed at highly substantive oil-in-water emulsions comprising a polyhydroxlyated block polymer substantive agent having a $C_{12}$–$C_{20}$ ester chain. The substantive agent ester preferably is selected from the class consisting of oleates, palmitates, stearates and mixtures thereof. The polyhydroxylated portion of said substantive agent preferably comprises about 4–50 mol of ethylene glycol, more preferably about 20–40 mol of ethylene oxide, and most preferably about 30 mol of ethylene oxide.

More particularly, the present invention is directed at a substantive oil-in-water sunscreen composition having PEG 30 dipolyhydroxystearate present. The substantive oil-in-water sunscreen composition preferably comprises:

A. PEG 30 dipolyhydroxystearate;
B. one or more sunscreen agents of low water solubility;
C. one or more emulsifiers; and
D. water Additional compounds may be present to add cosmetic elegancy, color, and fragrance to the formulation. The substantive agent, such as PEG 30 dipolyhydroxystearate, preferably is present at a concentration of about 0.01 to about 10 percent by weight, more preferably at a concentration of about 3 to about 8 percent by weight of the total formulation. The water preferably comprises about 45 to about 75 percent by weight of the formulation.

The present invention also is directed at a low viscosity oil-in-water emulsion having improved stability comprising:

A. about 1 percent to about 35 percent of a sunscreen selected from octocrylene, octylsalicylate, homosalate, ethylhexyl-p-methoxy cinnamate, oxybenzone, avobenzone and menthyl anthranilate by weight; and
B. about 1 percent to about 8 percent by weight of a polyhydroxylated block polymer substantive agent.

The polyhydroxylated block polymer preferably comprises about 4–50 mol, more preferably about 20–40 mol, and most preferably about 30 mol of ethylene oxide. The preferred block polymer preferably further comprises a $C_{12}$–$C_{20}$ ester chain. In a preferred embodiment, the oil-in-water emulsion comprises:

A. about 3 to 27 percent sunscreen by weight; and
B. about 3 percent to about 8 percent by weight, more preferably about 3 to about 6 weight percent of the total composition, of PEG 30 dipolyhydroxystearate.

DETAILED DESCRIPTION OF THE INVENTION

The present invention is directed at an oil-in-water emulsion that is highly substantive, i.e. highly resistant to removal by water. In a preferred embodiment, the highly substantive emulsion is incorporated into a sunscreen formulation having good emulsion stability and cosmetic elegance, yet having a low viscosity. The highly substantive oil-in-water formulation comprises a polyhydroxylated block polymer, preferably with an ABA structure containing poly(hydroxylated ester) blocks and polyethylene glycol blocks. The fatty acid ester of this highly substantive emulsifying polymer generally has a $C_{12}$–$C_{20}$ chain length. The esters may be oleates, palmitates or stearates. The polyethylene glycol blocks of the highly substantive emulsifying agent preferably contain from about 4 to about 50 mol of ethylene oxide and more preferably from about 20 to about 40 mol of ethylene oxide. A particularly preferred compound is a polyethylene glycol dipolyhydroxystearate in which the polyethylene glycol contain 30 mol of ethylene glycol and is referred to as PEG 30 dipolyhydroxystearate. This product is manufactured by ICI Americas, a subsidiary of Imperial Chemical Industries PLC under the tradename Arlacel P-135. PEG 30 dipolyhydroxystearate, preferably is present in a concentration of about 0.01 to about 10.0 percent by weight based on the weight of the final formulation. In a more preferred embodiment, the PEG 30 dipolyhydroxystearate is present in a concentration of about 3 to about 8 percent of the total composition. The pH of the final formulation preferably is maintained between about 6 to about 10, more preferably between about 7 and about 9.

In addition to the polyhydroxylated block polymer described above, oil-in-water sunscreen formulations further comprise one or more UV-A and/or one or more UV-B additional actives, an additional emulsifier, emollient, humectant, dry-feel modifier, insect repellent, anti-microbial preservative, antioxidant, chelating agent, a pigment, and a fragrance.

Sunscreen Active Ingredients

The compositions of the present invention can contain a sunscreening effective amount of one or more oil-soluble sunscreening UV-B active agents or a mixture of one or more UV-B actives and one or more UV-A actives. UV-A sunscreening actives protect against long wavelength actinic radiation of the sun in the 320 to 400 nm range and UV-B sunscreening actives protect against shorter wavelength actinic radiation of the sun in the 290–320 nm range.

Typical sunscreen actives include: aminobenzoic acid at up to about 15 weight percent; cinoxate at up to about 3 weight percent; avobenzone at up to about 3 weight percent or about 2 to 3 percent in admixture with one or more other sunscreen active agents; diethanolamine methoxycinnamate at up to about 10 weight percent or about 8 to 10 percent in admixture; digalloyl trioleate at up to about 5 weight percent or about 2 to 5 percent in admixture; dioxybenzone at up to about 3 weight percent alone or in admixture; ethyl 4-[bis(hydroxypropyl)]-aminobenzoate at up to about 5 weight percent or about 1 to 5 percent in admixture; glyceryl aminobenzoate at up to about 3 weight percent or about 2 to 3 percent in admixture; homosalate at up to about 15 weight percent or about 4 to 15 percent in admixture; lawsone at up to about 0.25 weight percent, together with dihydroxyacetone at up to about 3 weight percent, alone or in admixture; menthyl anthranilate at up to about 5 weight percent or about 3.5 to 5 percent in admixture; octocrylene at up to about 10 weight percent or 7 to about 10 percent in admixture; octyl methoxycinnamate at up to about 7.5 weight percent or about 2 to 7.5 percent in admixture; ethylhexyl-p-methoxy cinnamate at up to about 7.5 weight percent; octyl salicylate at up to about 5 weight percent or about 3 to 5 percent in admixture; oxybenzone (benzophenone-3) at up to about 6 weight percent or about 2 to 6 percent in admixture; padimate O at up to about 8 weight percent or about 1.4 to 8 percent in admixture; phenylbenzimidazole sulfonic acid at up to about 4 weight percent or about 1 to about 4 percent in admixture; red veterinary petrolatum at up to about 100 percent or at least about 30 percent in admixture; sulisobenzone at up to about 10 weight percent or about 5 to 10 percent in admixture; titanium dioxide at up to about 25 weight percent or about 2 to 25 percent in admixture; and trolamine salicylate at up to about 12 weight percent or about 5 to 12 percent in admixture.

Preferred suitable UV-B sunscreening actives include octocrylene, also known as 2-ethylhexyl-2-cyano-3,3 diphenylacrylate available from Haarmann & Reimer, Springfield, N.J. U.S.A. under the tradename-Neo Heliopan Type 303; ethylhexyl-p-methoxycinnamate (also known as octyl-methoxy cinnamate) available from Givaudan-Roure Corporation, Specialty Division, Clifton, N.J., U.S.A. under the tradename Parsol MCX; octyl salicylate, also known as 2-ethylhexyl salicylate, available from Harmann and Riemer, under the tradename Neo Heliopan, Type OS; homosalate, also known as homomenthyl salate available from Universal Preserv-A-Chem Brooklyn, N.Y., U.S.A. under the tradename Uniderm Homosal.

Typical suitable UV-A sunscreening actives include; menthyl anthranilate, also known as menthyl-o-aminobenzoate, available from Haarmann & Reimer under the tradename Neo Helioplan Type MA; avobenzone, also known as butyl methoxydibenzoylmethane available from Givaudan- Roure Specialty Division under the tradename Parsol 1789; oxybenzone, also known as benzophenone 3, available from American Cyanamid Fine Chemicals Department Wayne N.J., U.S.A. under the tradename Spectra-Sorb UV-9 and benzophenone-8, also known as dioxybenzone, and available from American Cyanamid Fine Chemicals Department, Wayne N.J., U.S.A. under the tradename Spectra-Sorb UV-24.

Sunscreen emulsions containing mixtures of UV-B and UV-A sunscreen actives should be able to provide an SPF value between about 2 and about 50, or higher. Except as noted otherwise, one or more sunscreen actives can be employed in the present composition in amounts of from about 1 to about 35 weight percent, preferably about 1 to about 30 weight percent of the sunscreen composition, more preferably from about 3 to about 27 weight percent.

Emulsions/Emulsifiers

A stable emulsion is a mixture of two immiscible liquids, i.e. liquids that are not mutually soluble, but which can form a fluid in which very small droplets of one component are stably dispersed throughout the other liquid, giving the mixture the appearance of a homogeneous fluid. Emulsions can include particulate materials and materials which are solid or solid-like at room temperature, but which will liquefy at higher temperatures used during formation of the emulsion. The presence of an emulsifier enhances the ability of one of the immiscible liquids to remain in a continuous form, while allowing the other immiscible liquid to remain in a dispersed droplet form. Thus, one function of an emulsifier, a stabilizing compound, is to assist in the production of a stable emulsion. A secondary function of emulsifiers is to provide a thickening or "bodying" to an emulsion. Typically, emulsifiers are molecules with non-polar and polar parts that are able to reside at the interface of the two immiscible liquids. As used herein in reference to the emulsifiers, the term "HLB value" means the hydrophilic/lipophilic balance. The HLB value has been used by those skilled in the emulsion art as an approximate guide for selecting emulsifiers useful for preparing the various types of emulsions: emulsifiers having HLB values at least about 7 are commonly used to prepare oil-in-water emulsions.

An oil-in-water (o/w) emulsion is a mixture where water-insoluble droplets (the discontinuous phase) are dispersed in a continuous aqueous phase. A water-in-oil (w/o) emulsion is a mixture where water droplets (the discontinuous phase) are dispersed in a continuous oily phase. The composition of the present invention is an oil-in-water emulsion where the water-insoluble actives are dispersed in the oil phase, prior to mixture with the aqueous phase. The type of emulsion formed, oil-in-water (o/w) or water-in-oil (w/o), is sometimes determined by the volume ratio of the two liquids provided the ratio is sufficiently high. For example, with 5% by volume aqueous phase and 95% by volume oily phase (an oil:water phase ratio of 19), the emulsion likely will become w/o. For moderate ratios (such as <3), the type of emulsion is decided by several factors, such as order of addition or type of emulsifier. One liquid slowly added to a second liquid with agitation usually results in the second liquid being the continuous phase. Another factor is preferred solubility of the emulsifier, the phase in which the emulsifier is soluble most probably will be continuous.

Typical suitable emulsifiers having an HLB value about 1 to about 7 include, without limitation, sorbitan monooleate, sorbitan sesquioleate, sorbitan isostearate, sorbitan trioleate, PEG-22/dodecyl glycol copolymer, PEG-45/dodecyl glycol copolymer, polyglyceryl-3-diisostearate, polyglycerol esters of oleic/isostearic acid, polyglyceryl-6-hexaricinolate, polyglyceryl-4 oleate, polyglyceryl-4 oleate/PEG-8 propylene glycol cocoate, oleamide DEA, sodium glyceryl oleate phosphate and hydrogenated vegetable glycerides phosphate.

Emulsifiers which are soaps may be formed in-situ when their constituents (such as stearic acid and triethanolamine, which form TEA-stearate) are present together in the formulation. In addition, other anionic surfactants could be used, as well as non ionic and cationic surfactants. Examples include, without limitation, sorbitan esters such as sorbitan isostearate available as Crill 6, tradename of Croda Inc. of New York, N.Y. U.S.A.; polyglyceryl-3 distearate available as Cremophor GS-32, tradename of BASF, Parsippany, N.J. U.S.A.; and carbomer, which is a homopolymer of acrylic acid crosslinked with an allyl ether of sucrose, available as Carbopol 941, tradename of B. F. Goodrich, Cleveland, Ohio U.S.A. Other useful emulsifiers include ceteareth-15, cetyl alcohol, cetyl phosphate, dimethicone copolyol phosphate, glyceryl isostearate, hydrogenated lecithin, laureth-12, PEG-20 distearate, PEG-8 oleate, PEG-40 sorbitan diisostearate, polyglyceryl-10 distearate, polysorbate 20, polysorbate 80, PPG-7 lauryl ether, sodium laureth sulfate, sorbitan sesquioleate and acrylates/$C_{10-30}$ alkyl acrylate crosspolymer; these are only representatives from some of the useful emulsifier chemical classes.

During preparation of the emulsion, a base may be added to adjust the pH of the product. The sunscreen product typically has a pH of about 4 to about 10, more preferably about 6 to 9; most preferably the pH of the sunscreen is approximately neutral, i.e. about 7 to 9.

Conveniently, the total concentration of the emulsifiers used in the present invention in amounts ranges from about 0.05 to about 20 weight percent of the total composition, preferably from about 0.1 to about 15 percent, more preferably from about 7 to about 15 percent.

Water

Water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or composition can range from about 15 to 95 weight percent, preferably from about 45 to 75 percent.

Emollients

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil.

Other suitable emollients include squalane, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the sunscreen emulsion.

Humectants

A humectant is a moistening agent that promotes retention of water due to its hygroscopic properties. Suitable humectants include glycerin, polymeric glycols such as poyethylene glycol and polypropylene glycol, mannitol and sorbitol. One or more humectants can optionally be included in the in the sunscreen in amounts from about 1 to 10 weight percent.

Dry-feel Modifier

A dry-feel modifier is an agent which when added to an emulsion, imparts a "dry feel" to the skin when the emulsion dries. Dry-feel modifiers may also reduce sunscreen migration on the skin. Dry feel modifiers can include starches, talc, kaolin, chalk, zinc oxide, silicone fluids, inorganic salts such as barium sulfate, surface treated silica, precipitated silica, fumed silica such as an Aerosil® available from Degussa Inc. of New York, N.Y. U.S.A.

Waterproofing Agents

A waterproofing agent is a hydrophobic material that imparts film forming and waterproofing characteristics to an emulsion. PEG 30 dipolyhydroxystearate may be used alone or in combination with other suitable waterproofing agents, including copolymers derived from polymerization of octadecene-1 and maleic anhydride as disclosed in U.S. Pat. No. 4,522,807 is PA-18, tradename of the Chevron Chemicals Co., San Francisco, Calif. U.S.A. Another suitable waterproofing agent is a copolymer of vinyl pyrollidone and eicosene monomers such as Ganex Polymer, tradename of ISP Inc. of Wayne, N.J. U.S.A.

The waterproofing agent is used in amounts effective to allow the sunscreen to remain effective on the skin after exposure to circulating water for at least 80 minutes using the procedures described by the U.S. Food and Drug Administration in "Sunscreen Drug Products for OTC Human Use," Federal Register, Vol. 43, Aug. 25, 1978, Part 2, pp. 38206–38269.

Insect Repellents

Sunscreen products are typically used by persons contemplating outdoor activities, in which contact with bothersome or potentially harmful insects is possible. Therefore, it is frequently desired to incorporate one or more insect repelling agents into the products. The most widely used active ingredient for personal care products is N.N-Diethyl-m-toluamide, frequently called "DEET" and commercially available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more.

Antimicrobial Preservative

An antimicrobial preservative is a substance or preparation which destroys, or prevents or inhibits the proliferation of, microorganisms in the sunscreen composition, and which may also offer protection from oxidation. Preservatives are frequently used to make self-sterilizing, aqueous based products such as emulsions. This is done to prevent the development of microorganisms that may be in the product from growing during manufacturing and distribution of the product and during use by consumers, who may further inadvertently contaminate the products during normal use. Typical preservatives include the lower alkyl esters of para-hydroxybenzoates (parabens), especially methylparaben, propylparaben, isobutylparaben and mixtures thereof, benzyl alcohol, phenyl ethyl alcohol and benzoic acid. One or more antimicrobial preservatives can optionally be included in the sunscreen composition in an amount ranging from about 0.001 to about 10 weight percent, preferably about 0.05 to about 2 percent.

Antioxidants

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, vitamin E and vitamin C. One or more antioxidants can optionally be included in the sunscreen composition in an amount ranging from about 0.001 to about 5 weight percent, preferably about 0.01 to about 2 percent.

Chelating Agents

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.2 weight percent.

Fragrances

Fragrances are aromatic substances which can impart an aesthetically pleasing aroma to the sunscreen composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the sunscreen composition in an amount ranging from about 0.001 to about 10 weight percent, preferably about 0.01 to about 5 percent.

Dispensers

The present oil-in-water emulsion may be dispensed from many types of containers adapted for this purpose. The formulation preferably is delivered by a spray. The delivery means may comprise a manually actuated pump, or a pressurized container in which the emulsion is delivered by a propellant. A non-limiting example of a suitable container equipped with a dispensing means would be an 8 ounce round bottle equipped with a Eurogel type finger pump sold by Seaquist Perfect, a division of APTAGROUP, Cary, Ill., U.S.A.

Definitions and suppliers of many of the ingredients described above or used in the following illustrative examples may be found in J. M. Nikitakis, et al., Eds., CFTA International Cosmetic Ingredient Dictionary, Fourth Edition, The Cosmetic, Toiletry and Fragrance Association, Washington, D.C., (1991). Percentages disclosed herein are percent by weight, unless the context clearly indicates otherwise.

Examples 1–3 describe three highly substantive topical oil-in-water lotion formulations comprising PEG 30 dipolyhydroxystearate.

EXAMPLE 1

This example discloses an oil-in-water lotion having a waterproof SPF of 15

| INGREDIENT | QUANTITY |
| --- | --- |
| PART A | |
| Stearic Acid | 30.000 GM |
| Ethylhexyl-p-methoxycinnamate | 75.000 GM |
| Dicaprylyl maleate | 80.000 GM |
| Benzophenone 3 | 40.000 GM |
| Jojoba Oil | 0.5000 GM |
| Aloe Vera Lipoquinone | 0.5000 GM |
| Propylparaben, NF | 1.0000 GM |
| Phenyl Trimethicone | 5.0000 GM |
| Hydrogenated Vegetable Oil | 20.000 GM |
| PART B | |
| PEG-30 dihydroxystearate | 70.000 GM |
| Dimethicone | 4.0000 GM |
| Vit. E Acetate Cosmetic Grade | 1.0000 GM |
| PART C | |
| Silica Methyl Silylate | 10.0000 GM |
| PART D | |
| Water | 200.0000 GM |
| Acrylates/$C_{10}$–$C_{30}$alkyl acrylate crosspolymer | 1.7500 GM |
| PART E | |
| Water | 380.6500 GM |
| Sorbitol Solution, 70%, USP | 50.0000 GM |
| Triethanolamine, 99% NF | 22.5000 GM |
| Methylparaben, NF | 2.0000 GM |
| Disodium EDTA | 0.1000 GM |
| PART G | |
| Benzyl Alcohol, NF | 10.0000 GM |
| Fragrance | 6.0000 GM |
| PART H | |
| Water | 0.0000 MG |

The formulation of Example 1 is prepared as follows. Heat the ingredients in Part A to 170–180 F. while mixing. Add the PEG30 dihydroxystearate of Part B to Part A. Mix until dissolved. Add the dimethicone and vitamin E acetate and continue mixing. Add the silica methylsilylate of Part C. Continue mixing while maintaining the temperature at 170–180 F., until all the silica methyl silylate is dissolved.

To the water of Part D slowly sprinkle in the acrylates/$C_{10}$–$C_{30}$ alkylacrylate crosspolymer. Mix until the cross polymer is is wetted and the dispersion is homogeneous and lump-free. This dispersion is then added to Part E and heated to 170–180 F.

The hot oil phase comprising Parts A, B, and C at 170–180 F. is added to the mixture of Parts D and E at 170–180 F. while mixing. The formulation is allowed to cool. When the formulation has cooled to 120 F., Part G is added and cooling is continued until the formulation is at room temperature. When the formulation has cooled to room temperature, Q.S. to weight with the water of Part H, resume stirring, and mix well.

EXAMPLE 2

This example describes a topical oil-in-water formulation having a waterproof SPF of 30.

| INGREDIENT | QUANTITY |
| --- | --- |
| PART A | |
| Stearic Acid | 20.0000 GM |
| Ethylhexyl-p-methoxycinnamate | 75.0000 GM |
| Homomenthyl Salicylate; Homosal | 80.0000 GM |
| Benzophenone 3 | 40.0000 GM |
| Jojoba Oil | 0.50000 GM |
| Aloe Vera Lipoquinone | 0.50000 GM |
| Propylparaben, NF | 1.0000 GM |
| Phenyl Trimethicone | 5.0000 GM |
| Hydrogenated Vegetable Oil | 20.0000 GM |
| PART B | |
| PEG-30 dihydroxystearate | 70.0000 GM |
| Dimethicone | 4.0000 GM |
| Vitamin E Acetate Cosmetic Grade | 1.0000 GM |
| PART C | |
| Silica Methyl Silylate | 10.0000 GM |
| PART D | |
| Water | 200.0000 GM |
| Acrylates/$C_{10}$–$C_{30}$alkyl acrylate crosspolymer | 1.7500 GM |
| PART E | |
| Water | 380.6500 GM |
| Sorbitol Solution, 70%, USP | 50.0000 GM |
| Triethanolamine, 99% NF | 22.5000 GM |
| Methylparaben, NF | 2.0000 GM |
| Disodium EDTA | 0.1000 GM |
| PART G | |
| Benzyl Alcohol, NF | 10.0000 GM |
| Fragrance | 6.0000 GM |
| PART H | |
| Water | 0.0000 MG |

The formulation of Example 2 is prepared in the following manner. Heat the ingredients of Part A to 170–180 F. while mixing. Add the PEG 30 dihydroxystearate of Part B to Part A and mix until dissolved. Add the dimethicone and the vitamin E acetate and continue mixing. Next add the silica methylsilylate of Part C to Parts A and B. Continue mixing while maintaining the temperature at 170–180 F., until all the silica methyl silylate is dissolved.

To the water of Part D, slowly sprinkle in the acrylates/$C_{10}$–$C_{30}$ alkylacrylate crosspolymer and mix until the crosspolymer is wetted and the dispersion is homogeneous and lump-free. Part D is then added to Part E and heated to 170–180 F.

The hot oil phase comprising Parts A, B and C at 170–180 F. is added to the hot water phase comprising Parts D and E at 170–180 F. while mixing is continued. The formulation is then allowed to cool. When the formulation has cooled to 120 F. Part G is added. The formulation is then cooled to room temperature. After the formulation has cooled to room temperature, Q.S. to weight with the water of Part H, resume stirring and mix well.

EXAMPLE 3

This example describes a topical oil-in-water lotion having a waterproof SPF of 45.

| INGREDIENT | QUANTITY |
| --- | --- |
| PART A | |
| Stearic Acid | 20.0000 GM |
| Ethylhexyl-p-methoxycinnamate | 75.0000 GM |
| Homomenthyl Salicylate; Homosal | 80.0000 GM |
| Benzophenone 3 | 60.0000 GM |
| Jojoba Oil | 0.5000 GM |
| Aloe Vera Lipoquinone | 0.5000 GM |
| Propylparaben, NF | 1.0000 GM |
| Phenyl Trimethicone | 5.0000 GM |
| Hydrogenated Vegetable Oil | 20.0000 GM |
| PART B | |
| PEG-30 dihydroxystearate | 50.0000 GM |
| Dimethicone | 4.0000 GM |
| Vit E Acetate Cosmetic Grade | 1.0000 GM |
| PART C | |
| Silica Methyl Silylate | 10.0000 GM |
| PART D | |
| Water | 200.0000 GM |
| Acrylates/$C_{10}$–$C_{30}$alkyl acrylate crosspolymer | 1.7500 GM |
| PART E | |
| Water | 380.6500 GM |
| Sorbitol Solution, 70%, USP | 50.0000 GM |
| Triethanolamine, 99% NF | 22.5000 GM |
| Methylparaben, NF | 2.0000 GM |
| Disodium EDTA | 0.1000 GM |
| PART F | |
| Benzyl Alcohol, NF | 10.0000 GM |
| Fragrance | 6.0000 GM |
| PART G | |
| Water | 0.0000 MG |

The formulation of Example 3 was prepared in the following manner. Heat the ingredients of Part A to 170–180 F. while mixing. Add the PEG 30 dihydroxystearate of Part B to the hot oil phase of Part A and mix until the dihydroxystearate is dissolved. Add the dimethicone and vitamin E acetate of Part B and continue mixing. Next add the silica methyl silylate of Part C to Parts A and B. Continue mixing while maintaining the temperature at 170–180 F., until all the silica methyl silylate is dissolved.

To the water of Part D, slowly sprinkle in the acrylates/$C_{10}$–$C_{30}$ alkylacrylate crosspolymer and mix until the crosspolymer is wetted and the dispersion is homogeneous and lump-free. This dispersion is then added to the ingredients of Part E and heated to 170–180 F.

The hot oil phase comprising Parts A, B and C at 170–180 F. is then added to the hot water phase comprising Parts D and E at 170–180 F. while mixing. The formulation is then allowed to cool. When the formulation has cooled to 120 F., Part G is added. The formulation is then cooled to room temperature. After the formulation has cooled to room temperature, Q.S. to weight with the water of Part G, resume stirring and mix well.

The following examples, Examples 4–6, describe highly substantive, stable oil-in-water sunscreen formulations having relatively low viscosities which may be adapted for dispensing from a pump spray device.

EXAMPLE 4

This examples describes a pump spray lotion having a waterproof SPF of 30.

| INGREDIENT | QUANTITY |
| --- | --- |
| PART A | |
| Stearic Acid | 16.0000 GM |
| Ethylhexyl-p-methoxycinnamate | 75.0000 GM |
| Octocrylene | 100.0000 GM |
| Benzophenone 3 | 60.0000 GM |
| Jojoba Oil | 0.5000 GM |
| Aloe Vera Lipoquinone | 0.5000 GM |
| Propylparaben, NF | 1.0000 GM |
| Phenyl Trimethicone | 4.0000 GM |
| Hydrogenated Vegetable Oil | 16.0000 GM |
| Vit E Acetate Cosmetic Grade | 1.0000 GM |
| PART B | |
| PEG-30 dihydroxystearate | 56.0000 GM |
| Dimethicone | 3.0000 GM |
| PART D | |
| Water | 589.1000 GM |
| Acrylates/$C_{10}$–$C_{30}$ alkyl acrylate crosspolymer | 1.8000 GM |
| PART E | |
| Sorbitol Solution, 70%, USP | 40.0000 GM |
| Triethanolamine, 99% NF | 18.0000 GM |
| Methylparaben, NF | 2.0000 GM |
| Disodium EDTA | 0.1000 GM |
| PART G | |
| Benzyl Alcohol, NF | 10.0000 GM |
| Fragrance | 6.0000 GM |
| PART H | |
| USP Purified Water | 0.0000 MG |

The formulation of Example 4 is prepared according to the following procedure. The ingredients of Part A are heated to about 170–180 degrees Fahrenheit with mixing. The PEG-30 dipolyhydroxystearate of Part B is added to the hot oil phase of Part A. Mixing is continued until all of the ingredients have been dissolved. The dimethicone of Part B is then added with mixing continuing.

The acrylates/$C_{10}$–$C_{30}$ alkyl acrylate crosspolymer are slowly sprinkled into the water of Part D. Mixing is continued until the crosspolymer is wetted and the dispersion is homogeneous and lump-free. The ingredients of Part E then are added to Part D and the mixture heated to about 170–180 degrees Fahrenheit.

The hot oil phase comprising Parts A and B at 170–180 F. is added to the hot water phase of parts D and E at 170–180 F. while mixing continues. The mixture is then allowed to cool. When the formulation has cooled to about 120 degrees Fahrenheit, the components of Part G are added, and the mixture subsequently allowed to cool to room temperature. Water of Part H is then added to raise the total weight of the formulation to 1 kg while mixing continues.

EXAMPLE 5

This example describes an pump spray lotion having a waterproof SPF of 40.

| INGREDIENT | QUANTITY |
| --- | --- |
| PART A | |
| Stearic Acid | 16.000 GM |
| Ethylhexyl-p-methoxycinnamate | 75.000 GM |
| Octocrylene | 100.0000 GM |
| Benzophenone 3 | 40.0000 GM |
| Jojoba Oil | 0.5000 GM |
| Aloe Vera Lipoquinone | 0.5000 GM |
| Propylparaben, NF | 1.0000 GM |
| Phenyl Trimethicone | 4.0000 GM |
| Hydrogenated Vegetable Oil | 16.0000 GM |
| Vitamin E, DL Alpha Tocopherol | 1.0000 GM |
| Butyl Methoxydibenzoylmethane | 20.0000 GM |
| PART B | |
| PEG-30 dihydroxystearate | 56.0000 GM |
| Dimethicone | 3.0000 GM |
| PART D | |
| USP Purified Water | 593.1000 GM |
| Acrylates/$C_{10}$–$C_{30}$ alkyl acrylate crosspolymer | 1.8000 GM |
| PART E | |
| Sorbitol Solution, 70%, USP | 40.0000 GM |
| Triethanolamine, 99% NF | 18.0000 GM |
| Methylparaben, NF | 2.0000 GM |
| Disodium EDTA | 0.1000 GM |
| PART G | |
| Benzyl Alcohol, NF | 10.0000 GM |
| Phenyl Ethyl Alcohol | 2.0000 GM |
| PART H | |
| USP Purified Water | 0.0000 MG |

The formulation of Example 5 is prepared as follows. Heat Part A to 170–180 F. while mixing. Add the PEG-30 dihydroxystearate of Part B to the hot oil phase of Part A. Mix until dissolved. Add dimethicone and continue mixing.

To the water of Part D, slowly sprinkle in the acrylates/$C_{10}$–$C_{30}$ alkyl acrylate crosspolymer. Mix until the crosspolymer is wetted and the dispersion is homogeneous and lump-free. Add to the ingredients of Part E and heat to 170–180 F.

Add the ingredients of Parts A and B at 170–180 F. to the ingredients of Parts D and E at 170–180 F. while mixing. Begin cooling to room temperature. Once the formula has cooled to 120 F., add part G. Continue cooling to room temperature. Once the formula cools to room temperature, Q.S. to weight with the water of Part H, resume stirring and mix well.

EXAMPLE 6

This example describes an oil-in-water lotion having a waterproof SPF of 50 which may be dispensed by a pump spray.

| INGREDIENT | QUANTITY |
| --- | --- |
| PART A | |
| Stearic Acid | 16.0000 GM |
| Ethylhexyl-p-methoxycinnamate | 75.0000 GM |
| Homomenthyl Salicylate; Homosal | 100.0000 GM |
| Benzophenone 3 | 40.0000 GM |
| Jojoba Oil | 0.5000 GM |
| Aloe Vera Lipoquinone | 0.5000 GM |
| Propylparaben, NF | 1.0000 GM |
| Phenyl Trimethicone | 4.0000 GM |
| Hydrogenated Vegetable Oil | 16.0000 GM |
| Vitamin E, DL Alpha Tocopherol | 1.0000 GM |
| Butyl Methoxydibenzoylmethane | 20.0000 GM |
| PART B | |
| PEC-30 dihydroxystearate | 56.0000 GM |

-continued

| INGREDIENT | QUANTITY |
| --- | --- |
| Dimethicone | 3.0000 GM |
| PART D | |
| USP Purified Water | 593.1000 GM |
| Acrylates/$C_{10}$–$C_{30}$ alkyl acrylate crosspolymer | 1.8000 GM |
| PART E | |
| Sorbitol Solution, 70%, USP | 40.0000 GM |
| Triethanolamine, 99% NF | 18.0000 GM |
| Methylparaben, NF | 2.0000 GM |
| Disodium EDTA | 0.1000 GM |
| PART G | |
| Benzyl Alcohol, NF | 10.0000 GM |
| Phenyl Ethyl Alcohol | 2.0000 GM |
| PART H | |
| USP Purified Water | 0.0000 MG |

The formulation of Example 6 is prepared as follows. Heat Part A to 170–180 F. while mixing. Add PEG 30 dihydroxystearate of Part B to the hot oil phase of Part A. Mix until dissolved. Add dimethicone and continue mixing.

To the water of Part D, slowly sprinkle in the acrylates/$C_{10}$–$C_{30}$ alkyl acrylate crosspolymer. Mixing until the crosspolymer is wetted and the dispersion is homogeneous and lump-free. Add to the ingredients of Part E and heat to 170–180 F.

Add the the ingredients of Parts A and B at 170–180 F. to the ingredients of Parts D and E at 170–180 F. while mixing. Begin cooling to room temperature. Once the formula has cooled to 120 F., add Part G. Continue cooling to room temperature. Once the formula cools to room temperature, Q.S. to weight with the water of Part H, resume stirring and mix well.

Numerous other variants of the above formulations will be apparent to one skilled in the art and within the spirit and scope of the invention.

What is claimed is:

1. A substantive oil-in-water sunscreen composition comprising:
   A. a substantive agent comprising a block polymer containing poly(hydroxylated ester) blocks and polyethylene glycol blocks;
   B. one or more oil soluble sunscreening UV-B active agents or a mixture of one or more UV-B actives and one or more UV-A actives;
   C. at least one emulsifier; and
   D. water.

2. The composition of claim 1 wherein the polyethylene glycol blocks of said substantive agent have from about 4 to about 50 mol of ethylene oxide.

3. The composition of claim 2 wherein the polyethylene glycol blocks of said substantive agent have from about 20 to about 40 mol of ethylene oxide.

4. The composition of claim 3 wherein the polyhydroxylated ester portion of said substantive agent is selected from the class consisting of oleates, palmitates, stearates and mixtures thereof.

5. The composition of claim 4 wherein the polyhydroxylated ester portion of said substantive agent has a $C_{12}$–$C_{20}$ chain length.

6. The composition of claim 5 wherein the substantive agent comprises PEG 30 dipolyhydroxystearate.

7. The composition of claim 6 wherein the PEG 30 dipolyhydroxystearate is present at a concentration of about 0.01 to about 10 percent by weight of the total composition.

8. The composition of claim 7 wherein the PEG 30 dipolyhydroxystearate is present at a concentration of about 3 to about 8 percent by weight of the total composition.

9. The composition of claim 8 wherein the oil soluble sunscreening active agent comprises a sunscreen selected from the class consisting of octocrylene, octylsalicylate, homosalate, ethylhexyl-p-methoxy cinnamate, oxybenzone, avobenzone and menthyl anthranilate.

10. The composition of claim 9 wherein the sunscreen comprises from about 1 percent to about 35 percent by weight of the total composition.

11. The composition of claim 10 wherein the sunscreen comprises from about 3 to about 27 percent by weight of the total composition.

12. The composition of claim 11 wherein the sunscreen comprises octocrylene.

13. The composition of claim 11 wherein the sunscreen comprises octylsalicylate.

14. The composition of claim 11 wherein the sunscreen comprises homosalate.

15. The composition of claim 11 wherein the sunscreen comprises ethyl-p-methoxycinnamate.

16. The composition of claim 11 wherein the sunscreen comprises oxybenzone.

17. The composition of claim 11 wherein the sunscreen comprises avobenzone.

18. The composition of claim 11 wherein the sunscreen comprises menthyl anthranilate.

19. A dermatologically compatible substantive sunscreening oil-in-water emulsion composition having a pH of about 6 to 10 comprising:
   A. about 1 percent to about 35 percent by weight of a sunscreen selected from octocrylene, octyl salicylate, homosalate, ethylhexyl-p-methoxy cinnamate, oxybenzone, avobenzone and menthyl anthranilate;
   B. about 3 percent to about 8 percent by weight of a substantive agent comprising a block polymer containing a poly(hydroxylated ester) block and a polyethelene glycol block;
   C. about 0.05 to about 20 percent by weight of an emulsifier; and
   D. about 45 to about 75 percent by weight water.

20. The composition of claim 19 wherein the polyethylene glycol block of said substantive agent comprises about 4 to about 50 mol ethylene oxide and wherein the poly (hydroxylated ester) block of said substantive agent comprises a $C_{12}$–$C_{20}$ chain length.

21. The composition of claim 20 wherein said substantive agent comprises PEG 30 dipolyhydroxystearate.

22. The composition of claim 21 wherein the sunscreen comprises about 3 percent to about 27 percent of the total composition by weight.

23. The composition of claim 22 wherein the PEG 30 dipolyhydroxystearate comprises about 3 to about 6 percent by weight of the total composition.

24. A dermatologically compatible substantive sunscreening oil-in-water emulsion for dispensing via a spray means comprising:
   A. about 1 percent to about 35 percent by weight of a sunscreen selected from octocrylene, octylsalicylate, homosalate, ethyl-p-methoxy cinnamate, oxybenzone, avobenzone and menthyl anthranilate; and
   B. about 1 percent to about 7 percent of a PEG 30 dipolyhydroxystearate.

25. The sunscreening oil-in-water emulsion of claim 24 wherein the sunscreen comprises about 3 to about 27 percent by weight of the total composition.

* * * * *